US010166261B2

(12) United States Patent
Majeed et al.

(10) Patent No.: US 10,166,261 B2
(45) Date of Patent: Jan. 1, 2019

(54) BACILLUS COAGULANS MTCC 5856 FOR THE MANAGEMENT OF MAJOR DEPRESSIVE DISORDER

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 15/198,158

(22) Filed: Jun. 30, 2016

(65) Prior Publication Data
US 2018/0000873 A1   Jan. 4, 2018

(51) Int. Cl.
*A61K 35/742* (2015.01)
*A61K 35/00* (2006.01)

(52) U.S. Cl.
CPC ........ *A61K 35/742* (2013.01); *A61K 2035/11* (2013.01)

(58) Field of Classification Search
None
See application file for complete search history.

(56) References Cited

U.S. PATENT DOCUMENTS

| | | | | |
|---|---|---|---|---|
| 8,192,733 B2 * | 6/2012 | Cobb | .................... | A61K 35/742 424/93.1 |
| 9,220,736 B2 * | 12/2015 | Farmer | ................. | A61K 35/742 |
| 9,579,352 B2 * | 2/2017 | Majeed | ................. | A61K 35/742 |
| 2016/0129054 A1 * | 5/2016 | Majeed | ................. | A61K 35/742 424/93.46 |

OTHER PUBLICATIONS

News Release by Massachusetts General Hospital. Nov. 2010; pp. 1-2 retrieved on Jun. 20, 2017 from webpage http://www.massgeneral.org/about/pressrelease.aspx?id=1307.*
Talarowska et al. "Myeloperoxidase gene expression and cognitive functions in depression". Adv Med Sci. Mar. 2015; 60(1):1-5; Epub Jun. 26, 2014.*
Diagnostic and Statistical Manual of Mental Disorders, 4th Edition (2000).
Friedrich et al., "Effects of Antidepressants in Patients With Irritable Bowel Syndrome and Comorbid Depression", Clinical Therapeutics (2010); 32(7):, 1221-1233.
Kim et al., "A randomized controlled trial of a probiotic, VSL#3, on gut transit and symptoms in diarrhoea-predominant irritable bowel syndrome", Alimentary Pharmacology and Therapeutics (2003); 17:895-904.
Bravo et al., "Ingestion of Lactobacillus strain regulates emotional behavior and central GABA receptor expression in a mouse via the vagus nerve", Proceedings of the National Academy of Sciences of the United States of America (2011); 108(38):16050-16055.
Kim et al., "A randomized controlled trial of a probiotic combination VSL# 3 and placebo in irritable bowel syndrome with bloating", Neurogastroenterology and Motility (2005); 17:687-696.
Jensen et al., "GanedenBC30™ cell wall and metabolites: anti-inflammatory and immune modulating effects in vitro", BMC Immunology (2010); 11:15.
Johns W.M., "A New Method for Measuring Daytime Sleepiness: The Epworth Sleepiness Scale", Sleep (1991);14(6):540-545.
Guidelines for the evaluation of probiotics in food, Joint FAO/WHO Working Group Report on Drafting Guidelines for the Evaluation of Probiotics in Food, London, Ontario, Canada, Apr. 30 and May 1, 2002.
Probiotics: In Depth/NCCIH, U.S. Department of Health and Human Services (http://www.hhs.gov/) National Institutes of Health (http://www.nih.gov/).
Indian Council of Medical Research/Department of Biotechnology, Ministry of Science and Technology, Government of India, New Delhi), ICMR-DBT Guidelines for Evaluation of Probiotics in Food, 2011).
Mannu et al., "Comparison of the incidence of virulence determinants and antibiotic resistance between Enterococcus faecium strains of dairy, animal and clinical origin", International Journal of Food Microbiology (2003); 88:291-304.
Rangel et al., "Epidemiology of *Escherichia coli* O157:H7 Outbreaks, United States, 1982-2002", Emerging Infectious Diseases (2005);11(4): 603-609.
Grozdanov et al., "Analysis of the Genome Structure of the Non-pathogenic Probiotic *Escherichia coli* Strain Nissle 1917", Journal of bacteriology (2004); 186: 5432-5441.
New study finds ProDURA Bacillus coagulans Demonstrates Superior heat resistance, University of Nebraska, http://valentuschoice.com/ProDura-Comparison.pdf, accessed on Sep. 24, 2018.
Muralidharan & Thajuddin, "Rapid differentiation of phenotypically and genotypically similar Synechococcus elongatus strains by PCR fingerprinting", Biologia (2011); 66(2): 238-243.

* cited by examiner

*Primary Examiner* — Vera Afremova

(57) ABSTRACT

The present invention discloses the use of probiotics for therapeutic management of major depressive disorder (MDD). Specifically, the invention discloses the method of therapeutically managing MDD in mammals with Irritable bowel syndrome using probiotic strain *Bacillus coagulans* MTCC 5856.

12 Claims, 7 Drawing Sheets

BACILLUS COAGULANS MTCC 5856 FOR THE MANAGEMENT OF MAJOR DEPRESSIVE DISORDER

BACKGROUND OF THE INVENTION

Field of the Invention

The invention in general relates to probiotics and their therapeutic potential. More specifically, the present invention relates to *Bacillus coagulans* MTCC 5856 for the treatment of major depressive disorder.

Description of Prior Art

Major depressive disorder (MDD) is characterized by increased medical morbidity, mortality, functional impairment, reduced quality of life, substantial health-care costs, and an increased risk of suicide, loss of interest or pleasure, disturbed sleep or appetite, low energy, and feelings of guilt or low self-worth (Greden et al, J Clin Psychiat. 2001, 62:26-31; Tranter et al, J Psychiat Neurosci. 2002, 27:241-247; Uher et al, Depress Anxiety. 2014, 31:459-471). MDD is one of the most common mental disorders worldwide, with a life time prevalence of 16.2% and a 12-month prevalence of 6.6% in developed countries (Trivedi et al, CNS Spectr. 2007, 12:1-27). According to the World Health Organization (WHO, 2010), MDD carries the heaviest burden of disability among mental and behavioural disorders. The findings from the 2014 National Survey on Drug Use and Health (NSDUH) revealed that in 2014, 11.4 percent of youths aged 12 to 17 (2.8 million adolescents) had a major depressive episode (MDE) in the past year (Center for Behavioral Health Statistics and Quality, 2015). Youths aged 12 to 17 in 2014 who had a past year MDE were more likely than those without a past year MDE to have used any illicit drugs in the past year (33.0 vs. 15.2 percent). Nierenberg and DeCecco concluded that though the initial antidepressant therapy reduces symptoms of depression in patients, but only 50-60% of patients with major depressive disorder respond to therapy (Nierenberg and DeCecco, J Clin Psychiat. 2001, 62:5-9). Furthermore, between 30 and 40% of patients who suffer from MDD never achieve symptom resolution with standard antidepressant treatment (Amsterdam and HornigRohan, Psychiatr Clin North Am. 1996, 19:371-386; Nierenberg and Amsterdam, J Clin Psychiat. 1990, 51:39-47). The association between MDD and altered gut microbiota is positioned within the concept of brain-gut microbe bidirectional signaling and its role in body homeostasis. A stable gut microbiota is cited to be essential for normal gut physiology and is believed to contribute to appropriate signaling along the brain-gut axis leading to the healthy status of an individual. Conversely intestinal dysbiosis can adversely influence gut physiology leading to inappropriate gut-brain signaling and associated deleterious consequences for normal CNS functions in individuals. (Sue Grenham et al, Front Physiol. 2011, 2:1-15). While in general it may be understood that "probiotics" are organisms or their substances that contribute to intestinal microbial balance thus conferring a health benefit to the host (FAO/WHO, 2002 in combination with Fuller R, Gut 1991, 32 (4): 439-442), and that the modification of microbial ecology by probiotic therapy may be used therapeutically for the management of stress responses and symptoms of anxiety and depression (Krabbe et al, Brain Behav Immun. 2005, 19:453-460; Ait-Belgnaoui et al, Psychoneuroendocrinology. 2012, 37:1885-95; De Palma et al, J Physiol. 2014, 592: 2989-2997), to produce an effective probiotic it is necessary to establish specificity of the microbes responsible for this effect in a fully conventional animal (Fuller R, Gut 1991, 32 (4): 439-442). Rather, a specific probiotic microbe, its ability to function as a protective gut microflora and further, its ability to confer a specific associated health benefit to an animal must be fully characterised and studied. Vasiljevic et al, Int. Dairy J. 2008, 18:714-728 indicated that the health benefits of probiotics are very strain specific and there is no single universal strain that would provide all proposed benefits and not all strains of the same species can effectively be used for treating against a defined health condition. The individual strains have to be tested for each property since probiotic properties are generally strain specific (Verdenelli et al, Eur J Nutr. 2009, 48(6):355-63). Probiotic effect for the production of a bioactive for specific immunomodulatory or neurological effects (Hyland & Stanton. Editor(s): The Gut-Brain Axis, (2016) 1st Edition: Dietary, Probiotic, and Prebiotic Interventions on the Microbiota), weight regulation (Million et al, Microb Pathog. 2013; 55:52-54.) are reported to be species and strain specific. Lack of complete evidence for each potential probiotic strain in terms of its protective effect and specific health benefit thereof is a technical problem in the field of probiotics therapy.

The present invention solves one such technical problem in establishing in vivo evidence for the protective effect of *Bacillus coagulans* MTCC 5856 in Irritable Bowel Syndrome (IBS) associated Major Depressive Disorder (MDD). It is thus the principle objective of the present invention to disclose the efficacy of *Bacillus coagulans* MTCC 5856 in ameliorating the symptoms of Major Depressive Disorder (MDD) in patients with Irritable Bowel Syndrome (IBS). While in the instant case, MDD associated with IBS is presented as an illustrative example, the invention also encompasses the therapeutic effect of *Bacillus coagulans* MTCC 5856 in the management of MDD in general.

The present invention fulfills the aforesaid objective and provides further related advantages.

SUMMARY OF THE INVENTION

The present invention discloses the use of *Bacillus coagulans* MTCC 5856 for therapeutic management of major depressive disorder (MDD). Specifically, the invention discloses the method of therapeutically managing MDD in mammals with Irritable Bowel Syndrome using *Bacillus coagulans* MTCC 5856.

Other features and advantages of the present invention will become apparent from the following more detailed description, taken in conjunction with the accompanying images, which illustrate, by way of example, the principle of the invention.

DESCRIPTION OF THE MOST PREFERRED EMBODIMENTS

Figure 1:
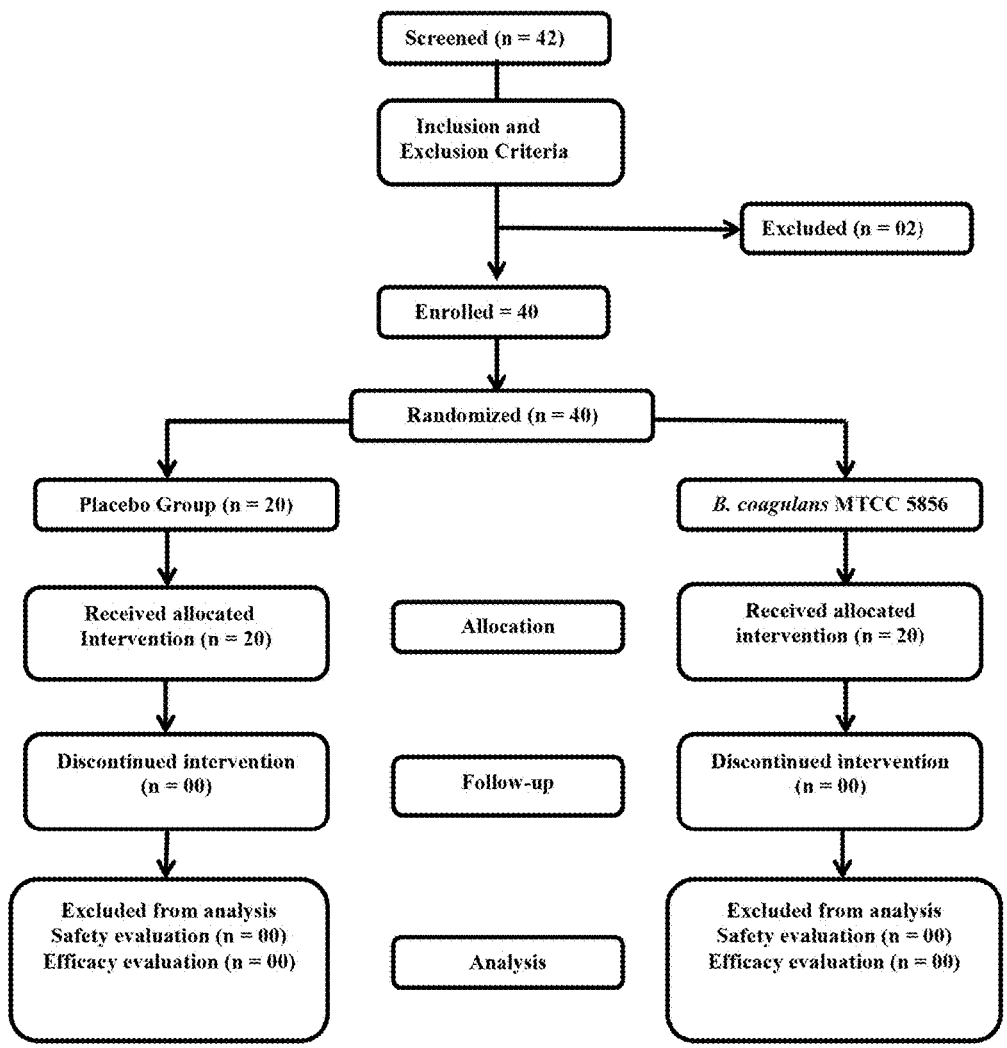
FIG. 1 shows the flowchart describing the procedures involved in the study.

In one most preferred embodiment, the present invention relates to a method of therapeutically managing major depressive disorder in mammals, said method comprising step of administering an effective dose of Bacillus coagulans MTCC 5856 to mammals experiencing symptoms of major depressive disorder. In a preferred embodiment, the present the invention relates to the use of Bacillus coagulans MTCC 5856 for therapeutic management of symptoms of major depressive disorder associated with Irritable Bowel Syndrome (IBS). In another preferred embodiment, Bacillus coagulans MTCC 5856 is administered at a dose of $2 \times 10^9$ cfu (spores)/day. In yet another preferred embodiment, the mammal is human. In further preferred embodiments, the symptoms of major depressive disorder are one selected from the group consisting of sleep disorder and dementia.

In an alternate most preferred embodiment, the present invention relates to a method of reducing serum myeloperoxidase levels in mammals experiencing symptoms of major depressive disorder said method comprising step of administering an effective dose of Bacillus coagulans MTCC 5856 to mammals experiencing symptoms of major depressive disorder. In preferred embodiments, the present the invention relates to the use of Bacillus coagulans MTCC 5856 for reducing serum myeloperoxidase levels in mammals experiencing symptoms of major depressive disorder associated with Irritable Bowel Syndrome (IBS). In another preferred embodiment, Bacillus coagulans MTCC 5856 is administered at a dose of $2 \times 10^9$ cfu (spores)/day. In yet another preferred embodiment, the mammal is human.

The specific examples included herein below illustrate the most preferred embodiments of the present invention.

EXAMPLE 1

Materials and Methods

Product Description

B. coagulans MTCC 5856 tablets (600 mg) contained 2 billion spores (333.33 mg), microcrystalline cellulose, starch, sodium starch glycolate and magnesium stearate. Placebo tablets contained dibasic calcium phosphate, microcrystalline cellulose, starch, and magnesium stearate, No differences in color, taste, texture or packaging were detectable between the two products. Tablets were sealed in identically-appearing, high-density polyethylene bottles with desiccant. Viable spore count of B. coagulans MTCC 5856 was determined by following pour plate method as per described previously (Majeed et al, Nutr J. 2016, 15:21). Analysis was performed twice in triplicate. Average means of spore viable counts was expressed in cfu/g.

Ethics and Informed Consent

This trial was conducted in accordance with the clinical research guidelines established by the Drugs and Cosmetics Act, 1940 of India, Drugs and Cosmetics Rules, 1945 of India, Ethical Guidelines for Biomedical Research on Human Participants, 2006 of Indian Council of Medical Research (ICMR) in India, the principles enunciated in the Declaration of Helsinki (Edinburgh, 2000) and the ICH—harmonized tripartite guideline regarding Good Clinical Practice (GCP). Written and oral information about the study in a language understandable by the subject was provided to all subjects. This study was registered at Clinical Trials Registry—India (www.ctri.nic.in) under the identifier CTRI/2015/05/005754 on 6 May 2015. There were no changes to the methods or planned endpoints after study initiation.

Participants

Subjects were included in the study if indicated "Yes" to all of the inclusion criteria and "No" to all of the exclusion criteria.

Inclusion Criteria.

(1) Male and/or female subjects ranging in age between 20 to 65 years. (2) Fulfilling Rome III Diagnostic Criteria (Drossman, Gastroenterology. 2006, 130:1377-1390) for Functional IBS (Functional Diarrhea). Criterion fulfilled for the last 3 months with symptom onset at least 6 months prior to diagnosis. (a) Recurrent abdominal pain or discomfort (uncomfortable sensation not described as pain) at least 3 days/month in the last 3 months associated with two or more of the following: (i). Improvement with defecation: (ii). Onset associated with a change in frequency of stool; (iii). Onset associated with a change in form (appearance) of stool; (b) Recurrent feeling of bloating or visible distension at least 3 days/month in the last 3 months; (c) Loose (mushy) or watery stools without pain occurring in at least 75% of stools. (3) Willingness to follow the protocol requirement as evidenced by written, informed consent. (4) Newly diagnosed patients with mild to moderate IBS in severity with possible sleep, pain and dementia associated comorbidities. (5) Willingness to complete subject diaries and study questionnaires. (6) Agree not to use any medication (prescription and over the counter), including vitamins and minerals, during the course of this study. (7) Agree not to use any yogurt during the course of this study. (8) Subjects whose blood chemistries are within a normal range or not considered clinically significant if outside the normal range. (9) Subject's assurance that they have not taken antibiotics or other Supplements whose primary site of action is in the GIT for a period up to 1 month prior to the start of the study. (10) Willing to come for regular follow-up visits.

Exclusion Criteria.

(1) Any clinically significant medical history, medical finding or an ongoing medical or psychiatric condition (other than depressive disorder/sleep disorder and dementia) exists which in the opinion of the investigator could jeopardize the safety of the subject, impact validity of the study results or interfere with the completion of study according to the protocol. (2) Significant abnormal findings as determined by baseline history, physical examination, vital signs (blood pressure, pulse rate, respiration rate) hematology, serum chemistry, urinalysis. (3) History or presence of significant alcoholism or supplement/drug abuse in the past one year. (4) Any medical or surgical conditions, which might significantly, interfere with the gastro intestinal tract, liver, kidneys, and/or blood-forming organs. (5) History of cardiovascular, renal, hepatic, asthma, glaucoma, pulmonary, neurologic, metabolic or psychiatric disease. (6) Participation in a clinical study during the preceding 90 days. (7) History of malignancy or other serious disease. (8) Any contraindication to blood sampling. (9) Smoking or Consumption of tobacco products. (10) Blood or blood products donated in past 30 days prior to study supplement administration. (11) Pregnant female subjects and lactating women. (12) Prior surgical therapy for obesity. (13) Patients using yogurt in their daily meal.

Trial Design

The disposition of the study participant shown in FIG. 1. This randomized, multicenter, double-blind, placebo controlled, parallel-group, clinical trial was conducted in 40 outpatient clinics and hospitals in India between April 2015 and October 2015. This clinical trial was conducted at three different sites [(i) Life Care Hospital, Bangalore, India. (ii) Sri Venkateshwara Hospital, Bangalore, India. (iii) Sapthagiri Institute of Medical Sciences and Research Center, Bangalore, India), The sample size of the study was 40, with 20 subjects randomized to each of the two study arms in a double-blinded manner at a 1:1 ratio. The subjects were blinded and received dosing as per randomization code provided at each site by an authorized person independently. Compliance with study supplement was reviewed at each visit. This was by examination of the returned supplement. All accountability records were incorporated into the investigator's study file. History of any medications being used currently were elicited and documented. The subjects were followed up regularly for all concomitant dosing from the time of screening till the follow up visit was captured and recorded. The patients were instructed against the use of any kind of yoghurt during the study duration. The daily food intake of the patients was recorded in the patient diaries provided to them at Visit 1 (Day 0). The same was checked and verified at subsequent visits by the investigators. The study consisted of a 90 day intervention period. Subjects met with the investigational team for screening, the baseline/randomization visit, day 30, day 60, day 90 and day 105. A description of Visits 1, 2, 3 and 4 with schedule of events are provided in Table 1.

TABLE 1

Schedule of events

| Procedure | Screening | Visit 1 (Day 0) Baseline | Visit 2 (Day 30) | Visit 3 (Day 60) | Visit 4 (Day 90) Final visit | Follow Up Visit (At least 15 days from the last visit) |
|---|---|---|---|---|---|---|
| Informed consent | X | | | | | |
| Medical history | X | | | | | |
| Physical examination | X | X | X | X | X | |
| Demographics [a] | X | X | X | X | X | |
| Vital Signs | X | X | X | X | X | |
| Hematology | X | | | | X | |
| Serum Chemistry | X | | | | X | |
| Myeloperoxidase [b] | | X | | | X | |
| Urine pregnancy test [c] | X | | | | | |
| Randomization | | X | | | | |
| IP Dispensing and Dosing | | X | X | X | | |
| Gastrointestinal Discomfort Questionnaire | | X | X | X | X | |
| Irritable Bowel SyndromeQuality of Life Questionnaire | | X | X | X | X | |
| HAM -D scale | | X | X | X | X | |
| MADRS | | X | X | X | X | |
| CGI-I & CGI-S | | X | X | X | X | |
| CES-D | | X | X | X | X | |
| Dementia checklist | | X | X | X | X | |
| Return of Unused IP | | | X | X | X | |

TABLE 1-continued

Schedule of events

| Procedure | Screening | Visit 1 (Day 0) Baseline | Visit 2 (Day 30) | Visit 3 (Day 60) | Visit 4 (Day 90) Final visit | Follow Up Visit (At least 15 days from the last visit) |
|---|---|---|---|---|---|---|
| Adverse events | | X | X | X | X | X |
| Concomitant medications | X | X | X | X | X | X |

[a] Age at screening only.
[b] Only for randomized subjects
[c] Urine pregnancy test at screening and on early termination, if any.

The assigned *B. coagulans* MTCC 5856 (LactoSpore®) study product was double blinded, i.e., neither the subjects nor the study staff knew the treatment group assigned until study completion. Double blinding was accomplished by independent blinding of the dosing bottles.

Intervention

Newly diagnosed patients who were not on any other treatment for major depression with IBS in the past 3 months were enrolled into the study. All enrolled subjects were asked to self administer one tablet per day (either *Bacillus coagulans* MTCC 5856 or Placebo) at least 30 minutes before a meal, in the morning as a dietary supplement for a period of 90 days.

Efficacy Outcomes

The primary outcome for this study was the mean 90 day change in depression and IBS symptoms as assessed by the Hamilton Rating Scale for Depression (HAM-D) (Friedrich et al, *Clin Ther.* 2010, 32: 1221-1233), Montgomery-Asberg Depression rating Scale (MADRS) Bravo et al, Proc Natl Acad Sci USA, 2011, 108: 16050-16055; Kim et al, Aliment Pharmacol Ther. 2003, 17:895-904), sleep quality and depressive symptom severity using 11-item Center for Epidemiological Studies-Depression Scale (CES-D) (Kim et al, Neurogastroenterol Motil. 2005, 17: 687-696) and Irritable Bowel Syndromequality of life questionnaire (IBS-QOL) (Tsuchiya et al, *Chin J Dig Dis.* 2004, 5:169-174). Additionally, secondary efficacy assessments included change in Clinical Global Impression-Improvement rating Scale (CGI-I) (Baron, *Postgrad Med.* 2009, 121: 114-118), Clinical Global Impression Severity rating Scale (CGI-S) (Baron, *Postgrad Med.* 2009, 121: 114-118), Dementia—Revised Memory and Behaviour Problem Checklist (RMBPC) (Jensen et al, *BMC Immunol.* 2010, 11:15), Gastrointestinal Discomfort Questionnaire (GI-DQ) (O'Mahony et al, *Gastroenterology.* 2005, 128: 541-551) and Modified Epworth Sleepiness Scale (mESS) (Johns, *Sleep.* 1991, 14: 540-545) from the baseline till the end of study as subjective test.

Bioassays

Along with subjective assessments (questionnaires), serum Myeloperoxidase, an inflammatory biomarker was also analysed for both the groups (*B. coagulans* MTCC 5856 and placebo) at the baseline and end of the study. Serum levels of myeloperoxidase in the blood samples were measured by the implementation of enzyme-linked immunosorbent assay (ELISA) techniques according to manufacturer directions. (Myeloperoxidase (human) EIA Kit, Code, 585001, Cayman Chemicals Company, Mich., USA)

Safety Outcomes

Safety of the study was assessed considering the occurrence of adverse events, safety blood parameters, and the follow-up of vital signs (blood pressure and heart rate). Laboratory data was summarized by presenting summary statistics of raw data and change from baseline values to end of study in laboratory values relative to normal reference limits. Descriptive physical examination such as abdomen, extremities, general appearance, head, ear, nose, throat, heart, lungs and neurological were monitored at the screening, day 0, day 30, day 60, day 90 and day 120 for the safety evaluation. Spontaneously reported or observed AEs were assessed at all post-screening study visits. AEs were evaluated in terms of intensity (mild, moderate, or severe) and possible relationship to the study product.

Data Reporting and Management

All data was reported in the respective hospital records that were then transcribed onto the Case Report Forms (CRFs). All data reported was first reviewed by the respective investigators present at the three sites and then entered by the clinical research coordinators onto the CRFs. This data entered in the CRFs was again verified by the investigators a second time. It was ensured that the source data matches with the data entered in the CRFs complying with the GCP guidelines on source data verification. Data collection during this clinical study and preparation of the data for analysis was conducted by separate and independent functional groups. Standard procedures ensured all CRFs are tracked and properly routed. The training of all the end users and clinical data management associates pertaining to the database entry and validation process was documented. The data entry operator transcribed the data from the paper CRF to the database. Data validation was conducted by the data manager. The database was locked post reconciliation of all data. The locked database was provided to the statistician who was independent of the study team. The data was then analyzed statistically.

Statistical Analysis

Statistical Analysis Software (SAS) of version 9.2 software was used for data analysis here. Paired 't' test, Analysis of Covariance (ANCOVA) and Wilcoxon signed rank sum test were used for appropriate data set variables to reach the best possible statistical conclusion between the *B. coagulans* MTCC 5856 receiving and Placebo receiving groups. The baseline descriptors were summarized as means and standard deviations for continuous variables and as frequencies and percentages for categorical variables. Last Observation Carry Forward (LOCF) method was followed for efficacy evaluations of subjects, whose data was not available in the last/final visit. No formal sample size calculation was performed.

Results

Patient Disposition and Characteristics

A total of 42 subjects were screened and 40 were enrolled into the study. There were no patient withdrawals or dropouts in this study. Out of 42 subjects screened, 40 were enrolled into the study and randomized into *B. coagulans* MTCC 5856 and placebo groups in 1:1 ratio. Treatment compliance across various visits and overall treatment compliance for the whole study indicates 24 (60%) patients met 100% treatment compliance on visit 4 (day 90) and on an average 66.7% met with 100% treatment compliance during the whole study period. At baseline visit (Day 0), no significant difference was observed between the two treatment groups in subject demographics (Table 2). On the day of screening, the mean age of all the enrolled subjects was 35.8±10.91, mean weight was 64.9±11.20 Kg and mean height was 158.8±8.24 cm. The mean BMI was 25.6±4.42 Kg/m$^2$ with 6 males (15%) and 34 females (85%) enrolled into the study. While one subject was non user of tobacco or tobacco products along alcoholic drinking history, 37 subjects (92.50%) were neither tobacco users nor alcoholic drinkers. Remaining subjects were occasional smokers and alcoholic drinkers. None of the enrolled subjects had abnormal medical history, except for gastro-intestinal. Around 03 subjects (7.50%) had earlier GI related medical history which had no interference with IBS. There was a statistically significant change (p<0.058) in the body weight in the group that received *B. coagulans* MTCC 5856 over placebo. However, no significant change in their respective BMI values was observed in both the groups.

TABLE 2

Demographics and Baseline Clinical Characteristics

| | Placebo (n = 20) | *B. coagulans* MTCC 5856 (n = 20) |
|---|---|---|
| Sex, n (%) | | |
| Female | 17 (85) | 17 (85) |
| Male | 03 (15) | 03 (15) |
| Age (years), mean (SD) | 43.88 ± 9.85 | 40.36 ± 10.28 |
| Height (cm), Mean(SD) | 157.39 ± 8.49 | 160.1 ± 7.87 |
| Body Mass Index (kg/m2) | 25.9 ± 4.49 | 25.4 ± 4.46 |
| Smokers, n (%) | | |
| Ex-Smoker | 18 (90) | 19 (95) |
| Non-Smoker | 01 (5) | 00 |
| Smoker | 01 (5) | 01 (5) |
| Race, n (%) | | |
| Central American | 00 | 00 |
| East Asian | 00 | 00 |
| South Asian | 20 (100) | 20 (100) |
| South American | 00 | 00 |
| South East Asian | 00 | 00 |
| Western European | 00 | 00 |
| White | 00 | 00 |
| Alcohol use | | |
| Non Drinker | 01 (5) | 00 |
| Past Drinker | 18 (90) | 19 (95) |
| Occasional Drinker | 01 (5) | 01 (5) |
| Current Drinker | 00 | 00 |
| Baseline data, mean (SD) | | |
| IBS-QOL | 102.6 ± 21.11 | 106.4 ± 23.44 |
| CGI-I | 3.8 ± 1.01 | 3.7 ± 0.87 |
| CGI-S | 3.7 ± 0.92 | 3.4 ± 0.96 |
| HAM-D | 14.5 ± 3.41 | 13.6 ± 4.41 |
| MADRS | 17.1 ± 4.63 | 16.3 ± 5.40 |
| CES-D | 20.7 ± 4.86 | 19.1 ± 5.25 |
| Dementia - Total frequency scoring | 61.3 ± 19.11 | 62.3 ± 17.08 |
| Dementia - Total reaction scoring | 61.0 ± 19.83 | 63.8 ± 17.57 |

TABLE 2-continued

Demographics and Baseline Clinical Characteristics

| | Placebo (n = 20) | *B. coagulans* MTCC 5856 (n = 20) |
|---|---|---|
| mESS | 10.9 ± 2.99 | 10.3 ± 2.43 |
| GI-DQ | 32.5 ± 13.88 | 30.1 ± 15.07 |

CES-D, Center for Epidemiological Studies Depression Scale;
CGI-I, Clinical Global Impression-Improvement rating Scale;
CGI-S, Clinical Global Impression Severity rating Scale;
CI, confidence interval
GI-DQ, Gastrointestinal Discomfort Questionnaire;
HAM-D, Hamilton Rating Scale for Depression;
IBS-QOL, Irritable Bowel Syndromequality of life questionnaire;
MADRS, Montgomery-Asberg Depression Rating Scale;
mESS, Modified Epworth Sleepiness Scale;
Values expressed as mean ± S.D Efficacy Evaluation As IBS symptoms are closely associated with clinical symptoms of depression, change in depression symptoms and IBS-quality of life were analyzed throughout the study period as primary efficacy measures. The 'p' value suggests that there was a statistically significant change in these symptoms from baseline to final visit, between the placebo and *B. coagulans* MTCC 5856 arms. At baseline visit (Day 0), no significant difference was observed between the two treatment groups in clinical characteristics (efficacy parameters) (Table 2). Statistical analysis using Analysis of Co-Variance (ANCOVA) showed the primary efficacy parameters were found to be statistically significant (p<0.01) between the *B. coagulans* MTCC 5856 and placebo groups (Table 3). This was largely the result of benefit in improving the symptoms of depression and IBS quality of life. The significant change in the score of HAM-D, MADRS, CES-D and IBS-QOL is the most relevant parameters to evaluate the clinical significance of depression and IBS (Friedrich et al, Clin Ther. 2010, 32: 1221-1233; Bravo et al, Proc Natl Acad Sci USA, 2011, 108: 16050-16055; Kim et al, Aliment Pharmacol Ther. 2003, 17:895-904; Kim et al, Neurogastroenterol Motil. 2005, 17: 687-696; Tsuchiya et al, Chin J Dig Dis. 2004, 5:169-174). Similarly, all secondary efficacy parameters were also found to be statistically significant between the *B. coagulans* MTCC 5856 and placebo groups except for "Dementia total reaction scoring" (Table 3).

TABLE 3

Summary of efficacy outcomes at the end of study (day 90): (full analysis set, last observation carried forward, ANCOVA model, 95% CI).

| Efficacy Parameters | Placebo (n = 20) | *B. coagulans* MTCC 5856 (n = 20) | p-value |
|---|---|---|---|
| Primary efficacy outcomes | | | |
| HAM-D | 12.5 ± 8.70 | 5.9 ± 4.88 | 0.007* |
| MADRS | 12.6 ± 8.00 | 6.0 ± 5.79 | 0.007* |
| CES-D | 16.7 ± 13.03 | 8.0 ± 6.17 | 0.013* |
| IBS-QOL | 84.1 ± 34.67 | 56.1 ± 31.26 | 0.0109* |
| Secondary efficacy outcomes | | | |
| CGI-I | 3.2 ± 1.09 | 2.3 ± 0.92 | 0.01* |
| CGI-S | 3.1 ± 1.05 | 2.3 ± 0.92 | 0.022* |
| Dementia - Total frequency scoring | 64.0 ± 28.26 | 45.9 ± 26.42 | 0.012* |
| Dementia - Total reaction scoring | 61.8 ± 29.94 | 51.6 ± 28.19 | 0.118 |

TABLE 3-continued

Summary of efficacy outcomes at the end of
study (day 90): (full analysis set, last observation
carried forward, ANCOVA model, 95% CI).

| Efficacy Parameters | Placebo (n = 20) | B. coagulans MTCC 5856 (n = 20) | p-value |
|---|---|---|---|
| GI-DQ | 22.9 ± 14.55 | 11.4 ± 18.23 | 0.045* |
| mESS | 8.9 ± 6.24 | 4.2 ± 3.92 | 0.01* |

Figure 2A:
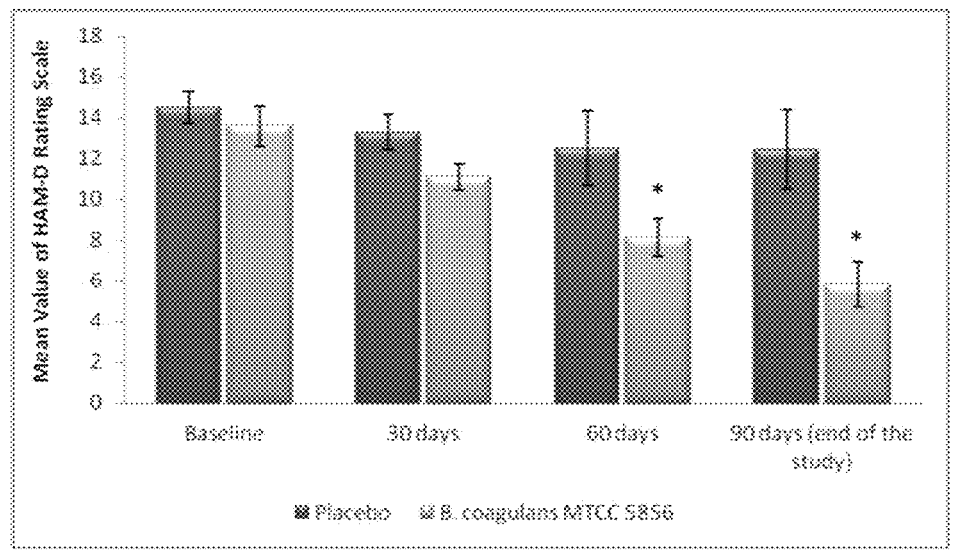
FIG. 2a shows the Hamilton Depression Rating Scale (HAM-D), for treatment (*B. coagulans* MTCC 5856) and placebo groups, on a scale of 0 to 20. All the values are expressed as mean±S.E. * indicate statistical significance (p<0.05) between placebo and treatment groups and also between baseline and 60th & 90th day of study.
Figure 2B:
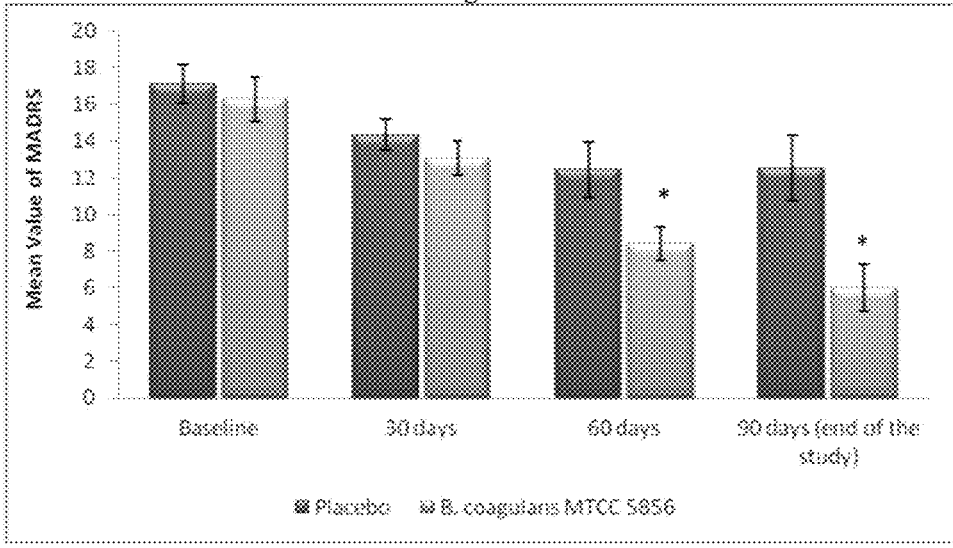
FIG. 2b shows the Montgomery-Asberg Depression rating for treatment (*B. coagulans* MTCC 5856) and placebo groups on a scale of 0 to 20. All the values are expressed as mean±S.E. * indicate statistical significance (p<0.05) between placebo and treatment groups and also between baseline and 60th & 90th day of study.
Figure 2C:
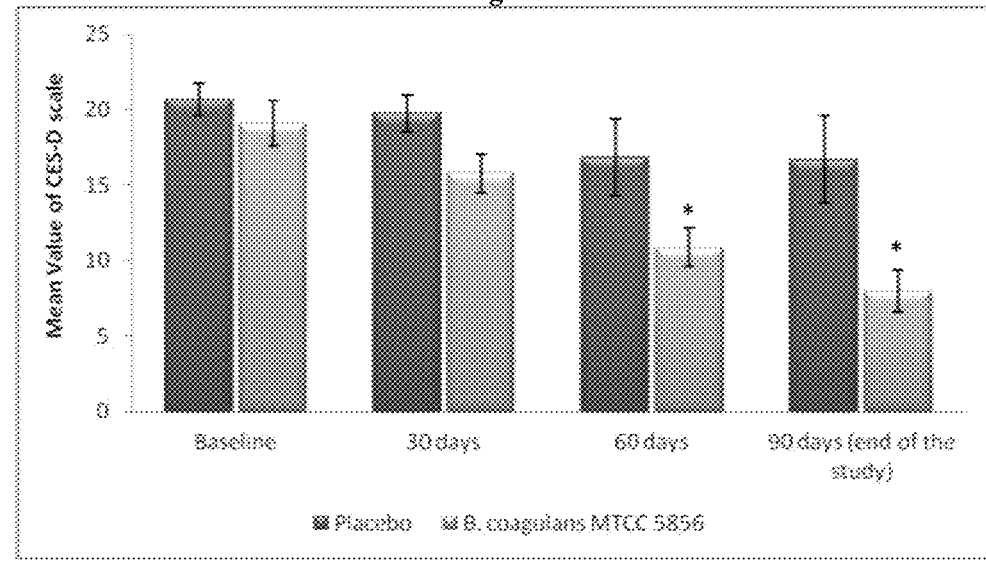
FIG. 2c shows the Center for Epidemiologic Studies Depression score for treatment (B. coagulans MTCC 5856) and placebo groups, on a scale of 0 to 30. All the values are expressed as mean±S.E. * indicate statistical significance (p<0.05) between placebo and treatment groups and also between baseline and 60th & 90th day of study.
Figure 2D:
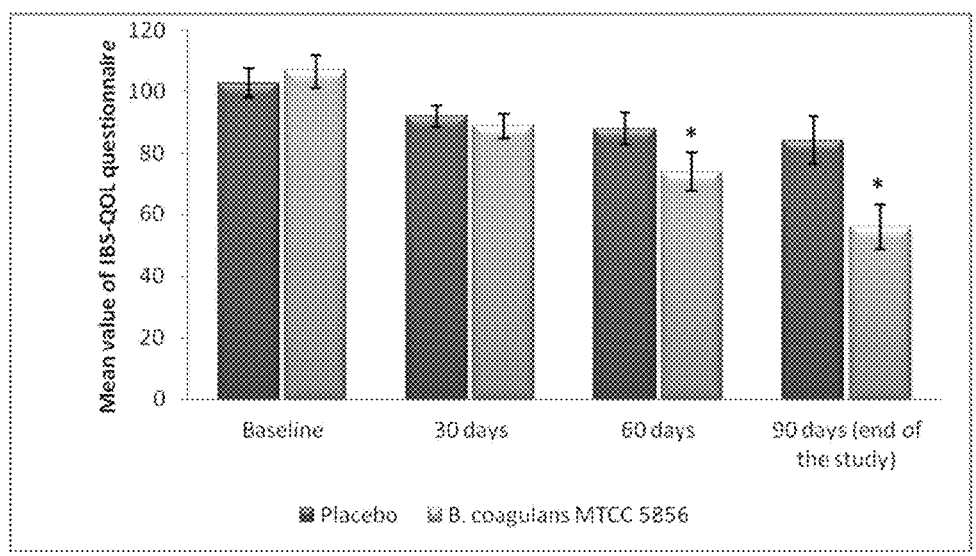
FIG. 2d shows the IBS—Quality of Life score for treatment (B. coagulans MTCC 5856) and placebo groups on a scale of 150. High QOL value indicates poor quality of life. All the values are expressed as mean±S.E. * indicate statistical significance (p<0.05) between placebo and treatment groups and also between baseline and 60th & 90th day of study.
Figure 3A:
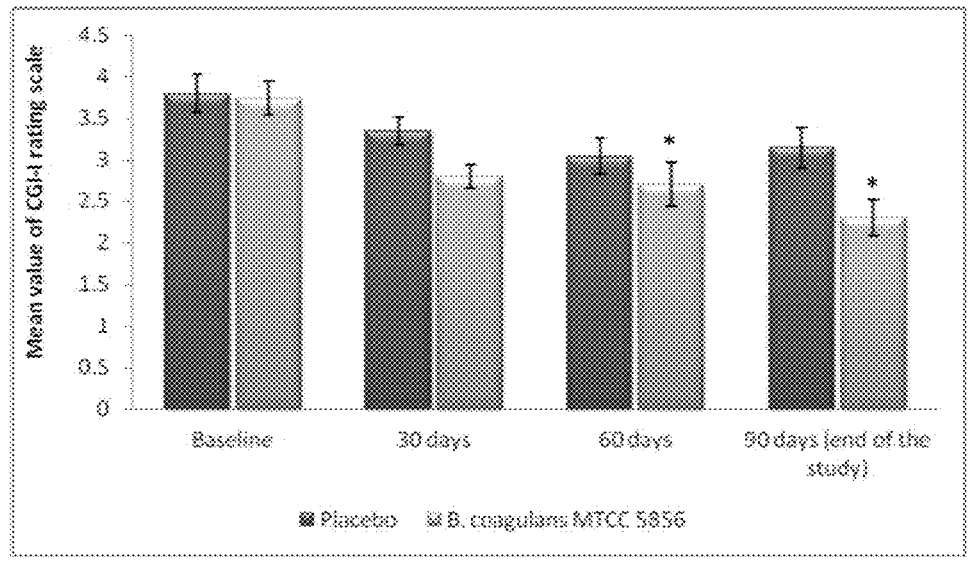
FIG. 3a shows the Clinical Global Impression—Improvement Rating for treatment (B. coagulans MTCC 5856) and placebo groups on a scale of 0 to 5. All the values are expressed as mean±S.E. * indicate statistical significance (p<0.05) between placebo and treatment groups and also between baseline and 60th & 90th day of study.
Figure 3B:
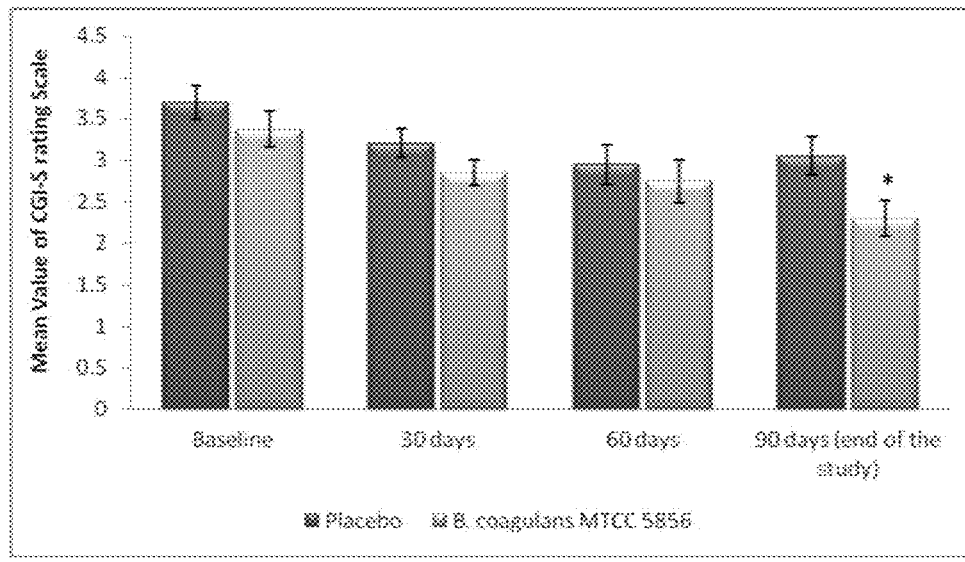
FIG. 3b shows the Clinical Global Impression—Severity Rating for treatment (B. coagulans MTCC 5856) and placebo groups on a scale of 0 to 5. All the values are expressed as mean±S.E. * indicate statistical significance (p<0.05) between placebo and treatment groups and also between baseline and 90th day of study.
Figure 3C:
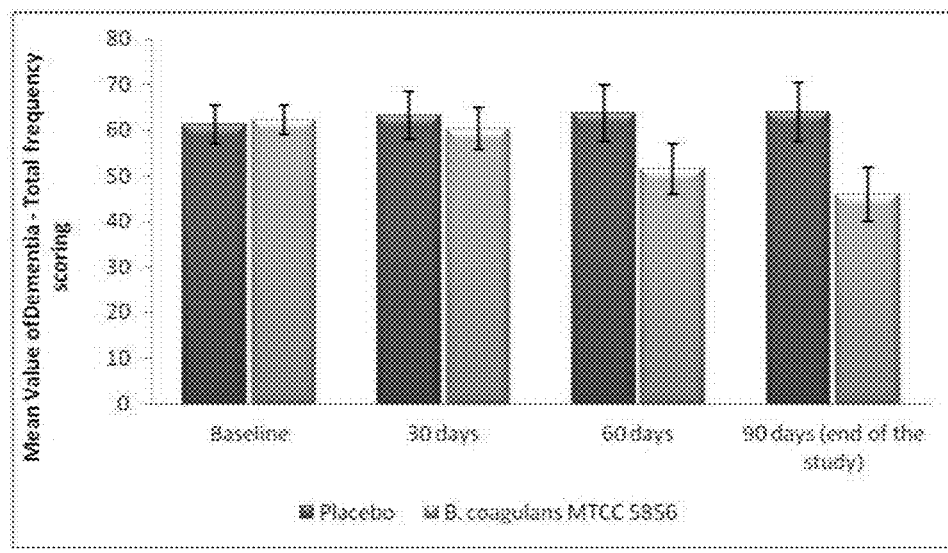
FIG. 3c shows the Dementia—Total Frequency Scoring for treatment (B. coagulans MTCC 5856) and placebo groups on a scale of 0 to 100. All the values are expressed as mean±S.E.
Figure 3D:
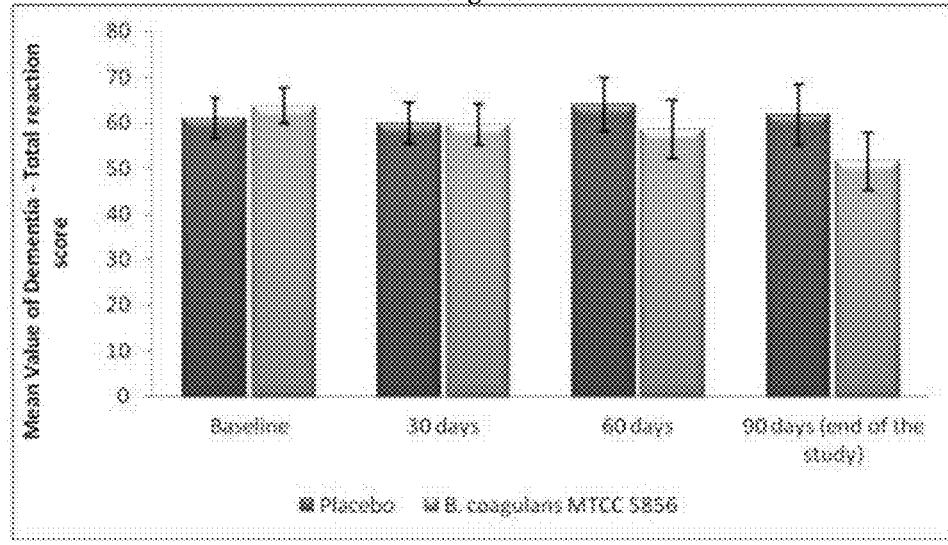
FIG. 3d shows the Dementia Total Reaction Scoring for treatment (B. coagulans MTCC 5856) and placebo groups on a scale of 0 to 100. All the values are expressed as mean±S.E.
Figure 3E:
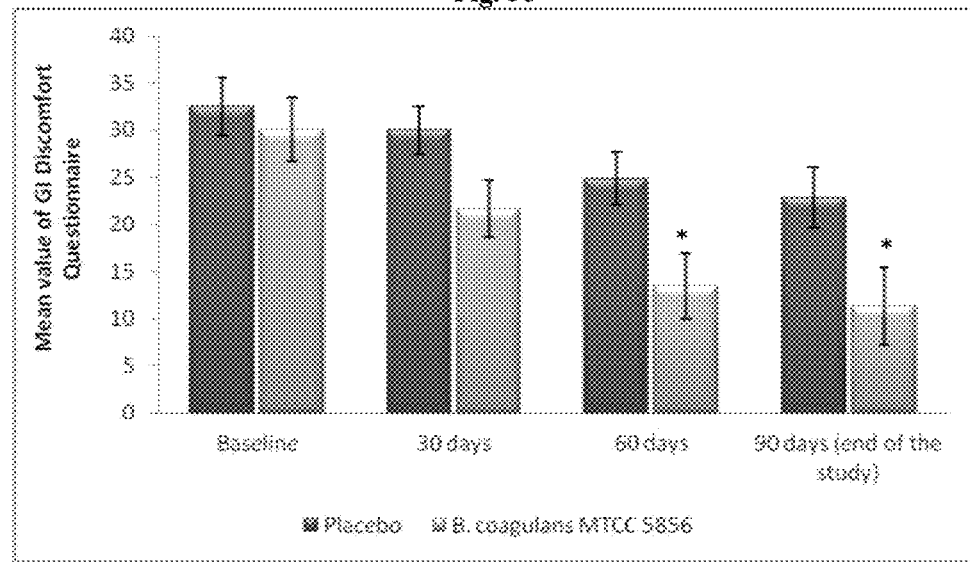
FIG. 3e shows the Gastrointestinal Discomfort Questionnaire for treatment (B. coagulans MTCC 5856) and placebo groups on a scale of 0 to 40. Low value indicates less GI discomfortness. All the values are expressed as mean±S.E. * indicate statistical significance (p<0.05) between placebo and treatment groups and also between baseline and 60th & 90th day of study.
Figure 3F:
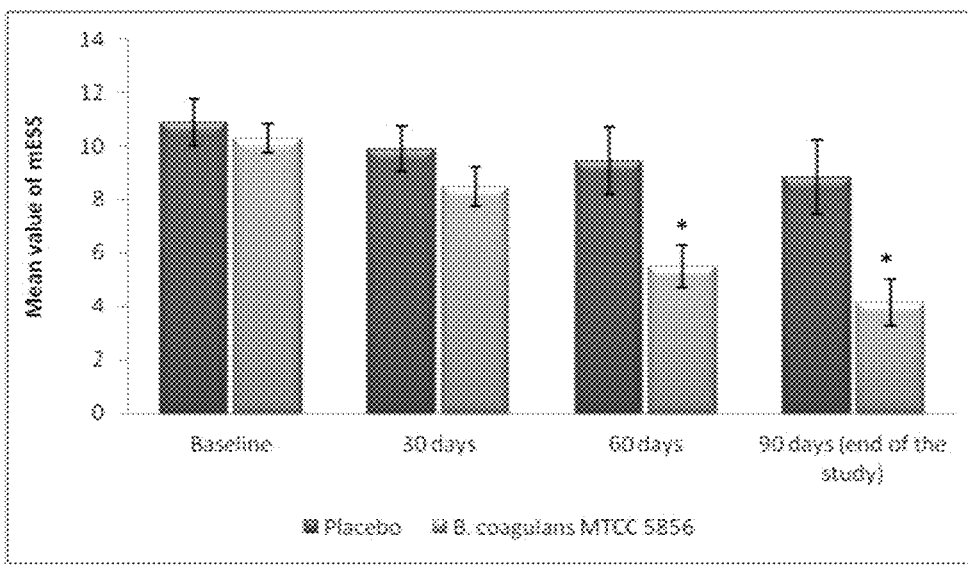
FIG. 3f shows the Modified Epworth Sleepiness Scale for treatment (B. coagulans MTCC 5856) and placebo groups on a scale of 0 to 15. All the values are expressed as mean±S.E. * indicate statistical significance (p<0.05) between placebo and treatment groups and also between baseline and 60th & 90th day of study.

ANCOVA, analysis of covariance;
CES-D, Center for Epidemiological Studies Depression Scale;
CGI-I, Clinical Global Impression-Improvement rating Scale;
CGI-S, Clinical Global Impression Severity rating Scale;
CI, confidence interval
GI-DQ, Gastrointestinal Discomfort Questionnaire;
HAM-D, Hamilton Rating Scale for Depression;
IBS-QOL, Irritable Bowel Syndromequality of life questionnaire;
MADRS, Montgomery-Asberg Depression Rating Scale;
mESS, Modified Epworth Sleepiness Scale;
*p value significant (<0.05)
Values expressed as mean ± S.D Furthermore, comparative mean values of efficacy assessments between *B. coagulans* MTCC 5856 and placebo groups across various visits (baseline, day 30, day 60 and day 90) are presented for primary efficacy parameters (FIGS. 2*a, b, c, d*) and secondary efficacy parameters (FIGS. 3*a, b, c, d, e, f*). Patients who were on *B. coagulans* MTCC 5856 had statistically significant difference for the efficacy parameters on day 60 and maintained till end of the study when compared with placebo (FIG. 2 and FIG. 3). *B. coagulans* MTCC 5856 was also found to be very beneficial for sleeplessness and to a less extent dementia in the current set of patients (Table 3 and FIGS. 3*c,d,f*).

Bioassay

Figure 4:
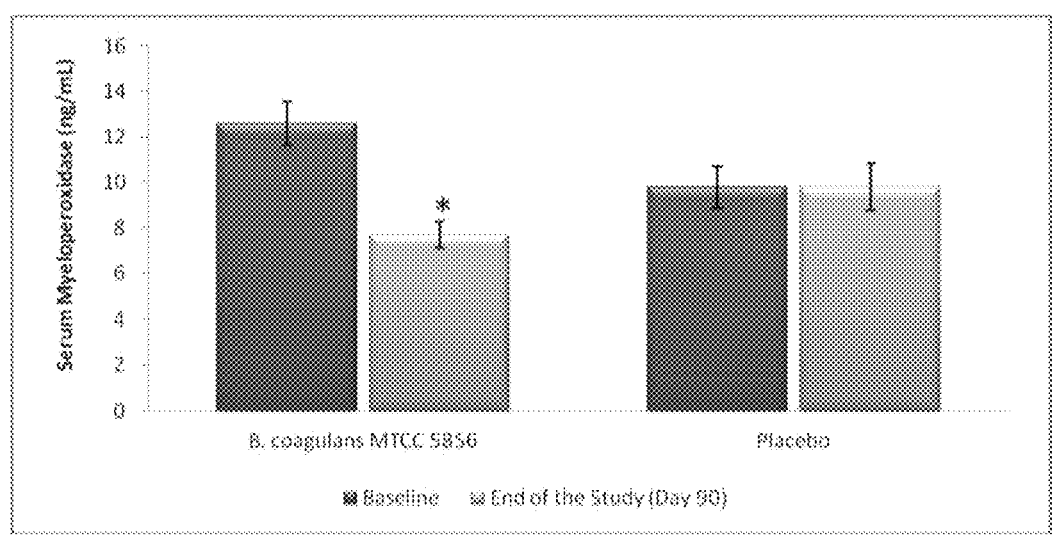
FIG. 4 shows the effect of B. coagulans MTCC 5856 supplementation on the serum myeloperoxidase activity. The figure also describes the serum myeloperoxidase activity at the baseline and end of the study (day 90) of both treatment and placebo groups. the values are expressed as mean±S.E. * indicate statistical significance (p<0.01) between the groups and also between baseline and end of the study (day 90).

The level of serum myeloperoxidase was significantly reduced from the baseline to the end of study (day 90) in patients receiving *B. coagulans* MTCC 5856 $2 \times 10^9$ spores (cfu)/day (p<0.01) (FIG. 4). However, no significant change of the level of serum myelo-peroxidase was observed in the placebo group (p>0.05) reduced from the baseline to the end of study (day 90) (FIG. 4).

Safety Evaluations

Vital signs such as Blood Pressure, Respiratory Rate, Pulse Rate and any abnormal lab/diagnostic parameters were considered for safety evaluations. No clinically significant changes were recorded for descriptive physical examination in both the group (*B. coagulans* MTCC 5856 and placebo group). Further, no clinically significant abnormal lab values (biochemistry and haematology) were identified and no statistically significant changes in the vitals were observed from the baseline to final visit (Table 4 and Table 5). There were no Serious Adverse Events or Significant Adverse Events noticed in this study. There was one adverse event reported with fever and weakness. The site investigator classified this adverse event as mild with no plausible relationship with the product and the adverse event reported to have been resolved without the use of any concomitant medication(s). The unblinding of study product code towards end of the study revealed that the patient with the adverse event belonged to the placebo group.

TABLE 4

Biochemistry and haematology values between two treatment groups

| Lab Parameter (Unit) | Visit | Placebo (n = 20) | B. coagulans MTCC 5856 (n = 20) | Normal range |
|---|---|---|---|---|
| Alanine aminotransferase (IU/L) | Screening | 22.6 ± 8.19 | 27.1 ± 15.30 | 0 to 41 |
| | Final Visit | 26.9 ± 26.87 | 31.0 ± 25.18 | |
| Albumin (g/dL) | Screening | 4.5 ± 0.33 | 4.6 ± 0.32 | 3.5 to 5.2 |
| | Final Visit | 4.4 ± 0.32 | 4.3 ± 1.01 | |
| Alkaline Phosphatase (U/L) | Screening | 206.2 ± 84.44 | 210.1 ± 97.16 | 53 to 128 |
| | Final Visit | 196.1 ± 72.90 | 214.3 ± 75.42 | |
| Aspartate aminotransferase (IU/L) | Screening | 25.1 ± 5.95 | 26.4 ± 7.00) | 0 to 40 |
| | Final Visit | 27.1 ± 16.69 | 27.3 ± 13.79 | |
| Blood urea nitrogen (mg/dL) | Screening | 12.9 ± 3.00 | 13.0 ± 5.87 | 5.0 to 24 |
| | Final Visit | 11.5 ± 2.75 | 11.4 ± 2.38 | |
| Fasting Blood Sugar (mg/dL) | Screening | 104.5 ± 51.03 | 114.1 ± 69.14 | 70 to 110 |
| | Final Visit | 105.9 ± 56.70 | 117.2 ± 78.78 | |
| LDL Cholesterol (mg/dL) | Screening | 121.6 ± 24.67 | 127.2 ± 42.56 | Up to 140 |
| | Final Visit | 123.0 ± 31.43 | 121.1 ± 44.51 | |
| Potassium (mEq/L) | Screening | 4.8 ± 0.41 | 4.7 ± 0.45 | 3.5 to 5.2 |
| | Final Visit | 5.7 ± 1.76 | 7.3 ± 7.44 | |
| Serum Creatinine (mg %) | Screening | 0.8 ± 0.12 | 1.2 ± 1.84 | 0.6 to 1.4 |
| | Final Visit | 1.2 ± 2.07 | 0.8 ± 0.12 | |
| Sodium (mEq/L) | Screening | 140.8 ± 2.63 | 133.2 ± 30.13 | 136 to 145 |
| | Final Visit | 138.5 ± 2.89 | 132.6 ± 21.55 | |
| Total Bilirubin (mg/dL) | Screening | 1.1 ± 0.44 | 1.4 ± 0.72 | 0.1 to 1.2 |
| | Final Visit | 1.3 ± 0.57 | 1.6 ± 1.14 | |
| Total Protein (g/dL) | Screening | 7.6 ± 0.53 | 7.6 ± 0.44 | 6.22 to 8.0 |
| | Final Visit | 7.4 ± 0.46 | 7.4 ± 0.56 | |
| Erythrocyte Count ($\times 10^6$ cells) | Screening | 4.4 ± 0.61 | 4.6 ± 0.53 | 4.0 to 6.5 |
| | Final Visit | 4.6 ± 0.65 | 4.6 ± 0.39 | |
| Haematocrit (%) | Screening | 37.9 ± 5.37 | 41.5 ± 3.60 | 40 to 50 |
| | Final Visit | 37.0 ± 5.63 | 38.1 ± 8.72 | |
| Haemoglobin (gm %) | Screening | 11.9 ± 2.00 | 13.2 ± 1.52 | 11 to 16 |
| | Final Visit | 11.7 ± 2.06 | 12.5 ± 2.15 | |
| Luekocyte Count (Cells cu. mm$^{-1}$) | Screening | 8562.5 ± 1930.07 | 9233.3 ± 2369.35 | 4000 to 11,000 |
| | Final Visit | 8575.0 ± 2879.49 | 8157.5 ± 2413.95 | |
| Platelet Count ($\times 10^5$ per cu. mm) | Screening | 2.7 ± 0.97 | 2.8 ± 0.80 | 1.5 to 4.5 |
| | Final Visit | 2.4 ± 0.91 | 2.3 ± 0.70 | |

Values expressed as mean ± S.D

TABLE 5

Change in mean Vital signs from baseline to the end of study (90 days)

| Vital Parameter | Supplements | Baseline | Day 90 (end of the study) | Change | p-value |
|---|---|---|---|---|---|
| Systolic Blood Pressure (mmHg) | B. coagulans MTCC 5856 | 122.5 | 121.0 | −1.50 | 0.2674 |
|  | Placebo | 123.5 | 120.0 | −3.50 | 0.0308 |
| Diastolic Blood Pressure (mmHg) | B. coagulans MTCC 5856 | 77.0 | 79.5 | 2.50 | 0.1713 |
|  | Placebo | 80.5 | 80.0 | −0.50 | 0.7157 |
| Pulse Rate (Beats per minute) | B. coagulans MTCC 5856 | 74.6 | 74.6 | 0.00 | 1.0000 |
|  | Placebo | 76.1 | 74.5 | −1.55 | 0.0841 |
| Heart Rate (Beats per minute) | B. coagulans MTCC 5856 | 74.7 | 74.8 | 0.10 | 0.8660 |
|  | Placebo | 75.8 | 74.8 | −1.00 | 0.1467 |
| Respiratory Rate (Breaths per minute) | B. coagulans MTCC 5856 | 21.1 | 21.1 | 0.00 | 1.0000 |
|  | Placebo | 21.4 | 20.8 | −0.60 | 0.1240 |
| Weight (kg) | B. coagulans MTCC 5856 | 65.7 | 66.7 | 1.04 | 0.0589* |
|  | Placebo | 63.1 | 64.0 | 0.91 | 0.0785 |
| Body Mass Index (kg/m$^2$) | B. coagulans MTCC 5856 | 25.6 | 25.7 | 0.01 | 0.8956 |
|  | Placebo | 25.7 | 25.8 | 0.01 | 0.8969 |

*p-value is estimated from Paired t-test, p < 0.05 considered as significant

CONCLUSION

The clinical study concluded that *Bacillus coagulans* MTCC 5856 at a dose of $2\times10^9$ spores (cfu) per day demonstrated efficacy for the treatment of patients experiencing symptoms of major depressive disorder associated with IBS. Furthermore, supplementation of *Bacillus coagulans* MTCC 5856 improved the depression and IBS symptoms which were also clinically meaningful. The data of the study concluded that *Bacillus coagulans* MTCC 5856 may be an alternative approach for the management of major depressive disorder in IBS patients.

While the invention has been described with reference to a preferred embodiment, it is to be clearly understood by those skilled in the art that the invention is not limited thereto. Rather, the scope of the invention is to be interpreted only in conjunction with the appended claims. In specific, it may be noted that while in the instant invention, MDD associated with IBS is presented as an illustrative example; the invention also encompasses the therapeutic effect of *Bacillus coagulans* MTCC 5856 in the management of MDD in general.

We claim:

1. A method of therapeutically managing dementia and dementia related sleep disorders presented as symptoms of major depressive disorder in human subjects, said method consisting step of administering *Bacillus coagulans* MTCC 5856 as a standalone, without co-administering with standard treatment of care, to the said subjects experiencing symptoms of major depressive disorder.

2. The method as in claim 1, wherein major depressive disorder is associated with Irritable Bowel Syndrome.

3. The method as in claim 1, wherein *Bacillus coagulans* MTCC 5856 is administered at a dose of $2\times10^9$ cfu (spores)/day.

4. A method of reducing serum myeloperoxidase levels in human subjects with dementia and dementia related sleep disorders presented as symptoms of major depressive disorder said method consisting step of administering *Bacillus coagulans* MTCC 5856 as a standalone, without co-administering with standard treatment of care, to said subjects experiencing symptoms of major depressive disorder.

5. The method as in claim 4, wherein major depressive disorder is associated with Irritable Bowel Syndrome.

6. The method as in claim 4, wherein *Bacillus coagulans* MTCC 5856 is administered at a dose of $2\times10^9$ cfu (spores)/day.

7. The method as in claim 1, wherein the standard treatment of care comprise drugs for the treatment of inflammatory bowel disease which include orally administering a combination of 30 mg of Domperidone and 40 mg of Esomeprazole together with 400 mg of Metronidazole once a day.

8. The method as in claim 4, wherein the standard treatment of care comprise drugs for the treatment of inflammatory bowel disease which include orally administering a combination of 30 mg of Domperidone and 40 mg of Esomeprazole together with 400 mg of Metronidazole once a day.

9. A method of therapeutically managing inflammatory bowel disease and its associated disease conditions said method consisting step of administering *Bacillus coagulans* MTCC 5856 as a standalone, without co-administering with standard treatment of care, to the said subjects experiencing symptoms of inflammatory bowel disease.

10. The method as in claim 9, wherein the associated disease conditions are selected from the group consisting of major depressive disorder, dementia and sleep disorders.

11. The method as in claim 9, wherein the standard treatment of care comprise drugs for the treatment of inflammatory bowel disease which include orally administering a combination of 30 mg of Domperidone and 40 mg of Esomeprazole together with 400 mg of Metronidazole once a day.

12. The method as in claim 9, wherein *Bacillus coagulans* MTCC 5856 is administered at a dose of $2\times10^9$ cfu (spores)/day.

* * * * *